United States Patent [19]

Sanaka

[11] Patent Number: 5,027,823
[45] Date of Patent: Jul. 2, 1991

[54] GAS FLOW VALVE, AND AUTOMATIC SPHYGMOMANOMETER USING SAME

[75] Inventor: Kohji Sanaka, Fujinomiya, Japan

[73] Assignee: Terumo Kabushiki Kaisha, Tokyo, Japan

[21] Appl. No.: 496,809

[22] Filed: Mar. 21, 1990

[30] Foreign Application Priority Data

Mar. 29, 1989 [JP] Japan .................................. 1-74892

[51] Int. Cl.⁵ .............................................. A61B 5/02
[52] U.S. Cl. ................................. 128/685; 137/513.5; 137/850
[58] Field of Search ................... 137/513.3, 513.5, 846, 137/850; 138/112, 113; 128/677, 679, 680, 685

[56] References Cited

U.S. PATENT DOCUMENTS 3,901,272  8/1975  Banners et al. ..................... 137/846
3,905,353  9/1975  Lichowsky .......................... 128/677

FOREIGN PATENT DOCUMENTS

3117546  10/1982  Fed. Rep. of Germany ...... 128/685
1194392  11/1985  U.S.S.R. .............................. 128/685

*Primary Examiner*—Stephen C. Pellegrino
*Assistant Examiner*—Robin R. Longo
*Attorney, Agent, or Firm*—Frishauf, Holtz, Goodman & Woodward

[57] ABSTRACT

A gas flow valve is provided in a pressure operated part to obtain an air flow velocity conforming to a change in pressure. A main body comprises a resilient member and is tapered from a base end to a distal end thereof to form a wedge-shaped portion at the distal end. In use, surfaces of the wedge-shaped portion serve as pressure-responsive surfaces, and gas is fed through a linear slit formed in the tip of the wedge-shaped portion and a passageway extending longitudinally within the main body and communicating with the slit. The slit is provided with a flapper comprising a thin sheet-like member formed to have a plurality of projections on a distal end thereof and oriented in such a manner that the projections are situated in the slit. Gaps are formed between the plurality of projections in the slit and serve as gas flow ports, and the slit is elastically deformed by a change in pressure received by the pressure-responsive surfaces, whereby the size of the air flow ports is varied and there is obtained an air flow velocity conforming to the change in pressure received by the pressure-responsive surfaces.

24 Claims, 6 Drawing Sheets

GAS FLOW VALVE, AND AUTOMATIC SPHYGMOMANOMETER USING SAME

BACKGROUND OF THE INVENTION

1. Field of the Invention

This invention relates to a gas flow valve and a sphygmomanometer using such a gas flow valve.

2. Description of the Prior Art

A conventional gas flow valve of this type has been disclosed in the specification of Japanese Utility Model Application Laid-Open (KOKAI) No. 61-142003 filed by the present applicant. This gas valve flow will be described with reference to the drawings.

Figure 13:
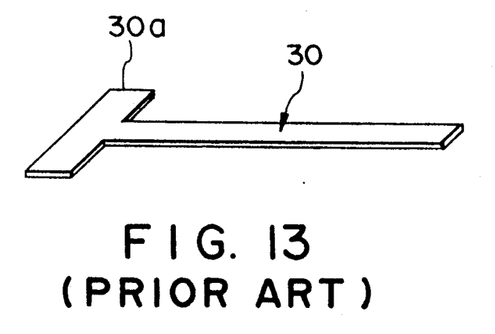
FIG. 13 is a perspective view showing a prior-art example of a flapper.
Figure 14:
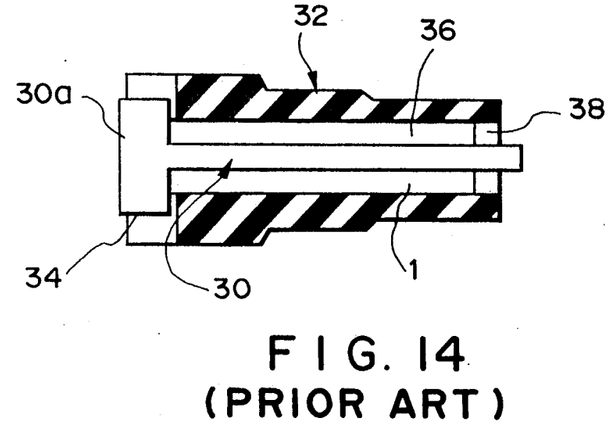
FIG. 14 is a sectional view showing a prior-art example of a gas flow valve.
Figure 15:
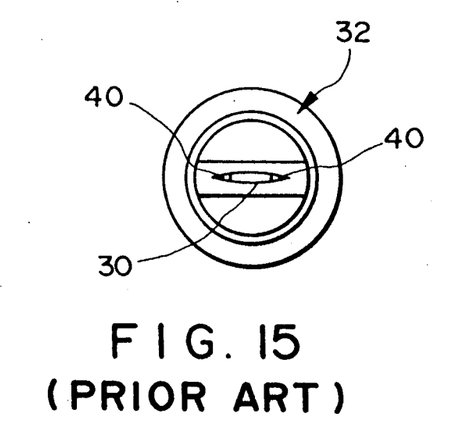
FIG. 15 is a front view of the valve shown in FIG. 14.

FIG. 13 is an external view of a flapper used in the prior-art gas flow valve of the present applicant, FIG. 14 is a plan view illustrating the main body of the prior-art gas flow valve the center of which is shown broken away, and FIG. 15 is a view showing the right side of FIG. 14.

As shown in FIG. 13, the flapper 30 has a generally T-shaped external form and is fabricated by machining a thin sheet. The flapper 30 is used mainly as a body for regulating the amount of leakage of gas flowing through the valve. Here the thin sheet constituting the flapper 30 is a thin piece of plastic or the like, the base end of which has a vane 30a projecting to the left and right at right angles to the longitudinal direction of the flapper 30.

As illustrated in FIG. 14, each vane 30a has a shape and dimensions that enable the vane 30a to fit into a groove 34 formed in a main body 32 of the gas flow valve. The longitudinal dimension of the flapper 30 is such that when the vane 30a is fitted in the groove 34 of main body 32, the distal end of the flapper 30 will pass through a linear opening or slit 38 provided in one end of the main body 32.

When the flapper 30 is received in an air passage 36 of the main body 32, as shown in FIG. 14, the slit 38 is opened so that gaps 40 are formed on both sides of the flapper 30. As a result, venting takes place through the gaps 40.

However, if the portion of the flapper 30 contacted and held by the slit 38 is made large in size in order to form the gaps 40 on both sides of the flapper 30 in this air flow valve using the conventional flapper, a variance in the shape of the slit 38 from one valve to another, which is ascribable to differences in the material forming the main body 32, has a greater effect, and therefore the performance of the air flow valve will also differ from one valve to another.

Furthermore, since the flapper 30 is not fixed sufficiently with respect to the main body 32, the flapper moves from side to side at the slit 38. Consequently, the velocity of gas flow is not consistent.

SUMMARY OF THE INVENTION

Accordingly, the present invention has been devised in view of the inconsistency in gas flow velocity encountered in the above-described conventional gas flow valve, and its object is to provide a gas flow valve which furnishes a stable gas flow velocity.

Another object of the present invention is to provide an automatic sphygmomanometer which uses this gas flow valve to make possible measurement based on a stabilized air flow velocity According to the present invention, the foregoing objects are attained by providing a gas flow valve comprising a resilient main body, used upon being accommodated in a tubular body, tapered from a base end to a distal end thereof to form a wedge-shaped portion at the distal end, with upper and lower surfaces of the wedge-shaped portion being made pressure-responsive surfaces and a tip of the wedge-shaped portion being formed to have a linear slit, a passageway extending longitudinally within the main body and communicating with the slit, and a thin sheet-like member formed to have a plurality of projections on a distal end thereof and disposed in the passageway in such a manner that the projections are situated in the slit, wherein gaps are formed between the plurality of projections in the slit and serve as gas flow ports, and the slit is elastically deformed by pressure received by the pressure-responsive surfaces, whereby the size of the air flow ports is varied.

In a preferred embodiment, the distal end portion of the thin sheet-like member is bifurcated and is held immobile by both inner edges of the slit, the thin sheet-like member is formed to have a substantially T-shaped vane portion for fixedly disposing the member in the passageway of the main body, and the vane portion is fixedly fitted into a groove of the main body.

In a preferred embodiment, the thin sheet-like member is made of a resin material.

In a preferred embodiment, the gas flow valve is disposed in a tubing system to construct a sphygmomanometer.

The pressure-responsive surfaces refer to surfaces designed to be capable of being deformed elastically by a change in received pressure. In a preferred embodiment, the distal end portion of the thin, sheet-like member is recessed and is embraced by the inner surface of the slit.

In the arrangement described above, the distal end of the thin, sheet-like member is divided into a plurality of projections and air flow ports are formed between the plurality of projections. As a result, deformable contact portions of the slit can be reduced, and the plurality of projections are clamped by the slit. This makes possible stabilized flow of gas.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

An embodiment of the present invention will now be described in detail with reference to the drawings.

Figure 1:
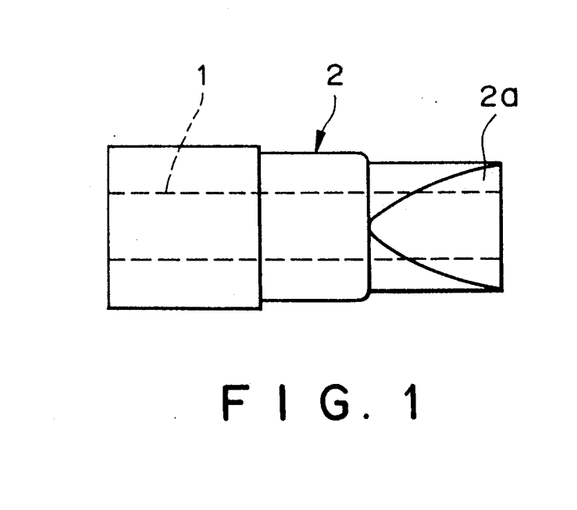
FIG. 1 is a plan view showing an embodiment of a gas flow valve according to the present invention.
Figure 2:
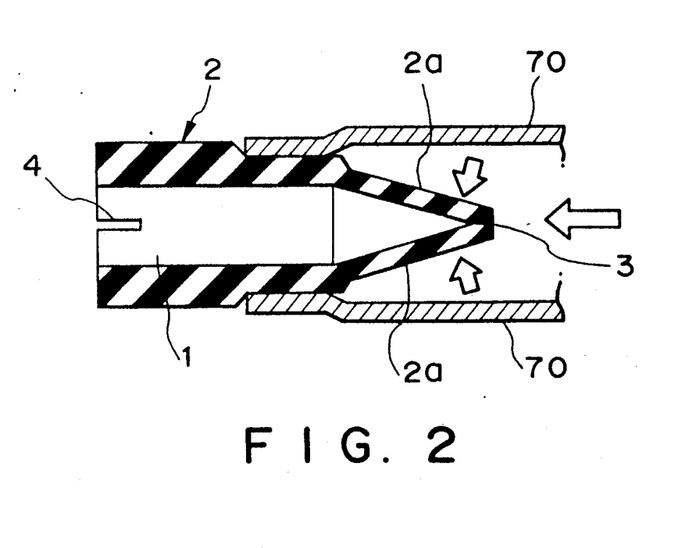
FIG. 2 is a sectional side view along the center of the valve of FIG. 1.
Figure 3:
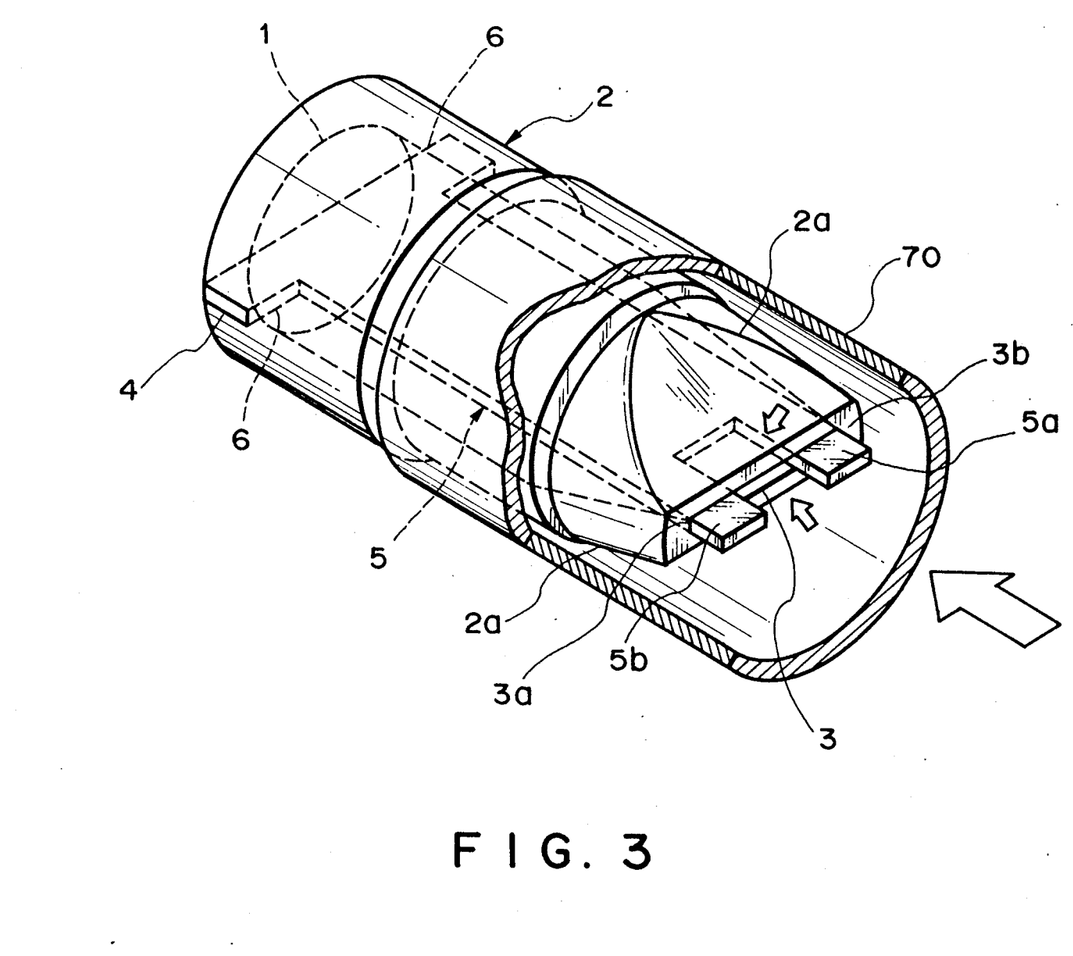
FIG. 3 is an external perspective view, partially cut away, showing the gas flow valve of FIGS. 1 and 2.
Figure 4:
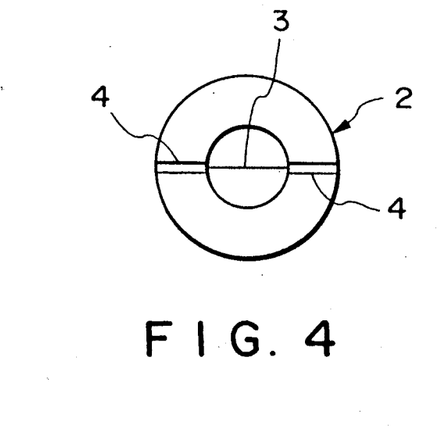
FIG. 4 is a left-side view of the valve shown in FIG. 1.

As shown in FIGS. 1, 2, 3 and 4, a gas flow valve has a main body 2 comprising a resilient material such as rubber. The main body 2 has an air passageway 1 (indicated by the broken lines in FIG. 1) and has its distal end tapered to define pressure-responsive surfaces 2a which form the distal end into a wedge-shaped configuration. As shown in FIG. 3, a linear slit 3 is formed at the terminus of the pressure-responsive surfaces 2a and is in communication with the air passageway 1.

A pair of grooves 4 are formed in the peripheral wall portion of an opening at the other end face of the main body 2. The grooves 4 are linear and cut in the same direction as the slit 3, and they extend into the main body 2 in the direction of the pressure-responsive surfaces 2a.

Figure 5:
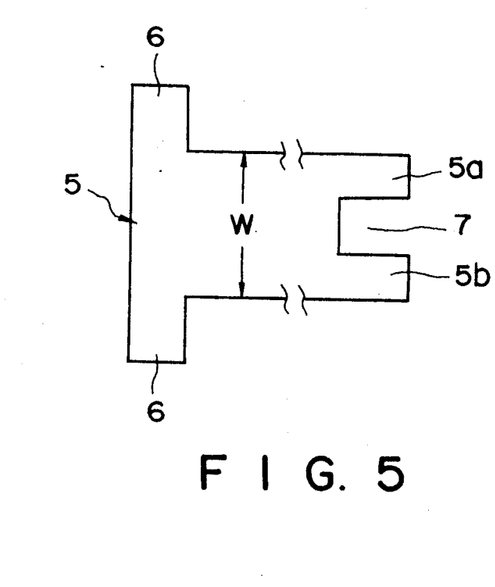
FIG. 5 is a plan view showing a flapper used by the valve of FIG. 1.

FIG. 5 is a plan view of a flapper 5 of the embodiment. The flapper 5, which is a thin, sheet-like member, is used in combination with the main body 2 described above. As shown in FIG. 5, vanes 6 for fixing the flapper to the main body 2 are formed integral with the base end portion of the flapper 5, and the vanes 6 extend transversely at right angles to the longitudinal direction of the flapper 5.

The distal end of the flapper 5 is divided into two projections 5a, 5b by a notch 7, as shown. The notch 7 defines a gap serving as a gas flow port when the flapper 5 is fitted into the main body 2 of the valve. It should be noted that the number of projections is not limited to two, for the distal end of the flapper can be divided into three or more projections by notches like the notch 7.

The width "W" of the flapper 5 should be such that the flapper 5 will be received in the slit 3 of main body 2 without clearance. In particular, the flapper 5 is designed to have a width such that the projections 5a, 5b of the flapper 5 will be grasped by the end portions of the slit 3 at its inner surface. The flapper 5, which is inserted into the flow passageway 1, has a length such that the distal end portion thereof will project somewhat from the slit 3. By virtue of this arrangement, the projections 5a, 5b of the flapper 5 within the slit 3 are retained by end portions of the slit 3 at the inner surface thereof.

As shown in FIGS. 2 and 3, the main body 2 constructed as described above is used upon being press-fitted into the end portion of a tubular body 70. Fluidic pressure applied in the direction of the arrow is received by the pressure-responsive surfaces 2a of the main body 2, as a result of which the slit 3 is deformed.

The operation of the gas flow valve constructed as set forth above will now be described based on an example in which the air flow valve is used as a constant-rate discharge valve in the air circuit of a sphygmomanometer.

Figure 6:
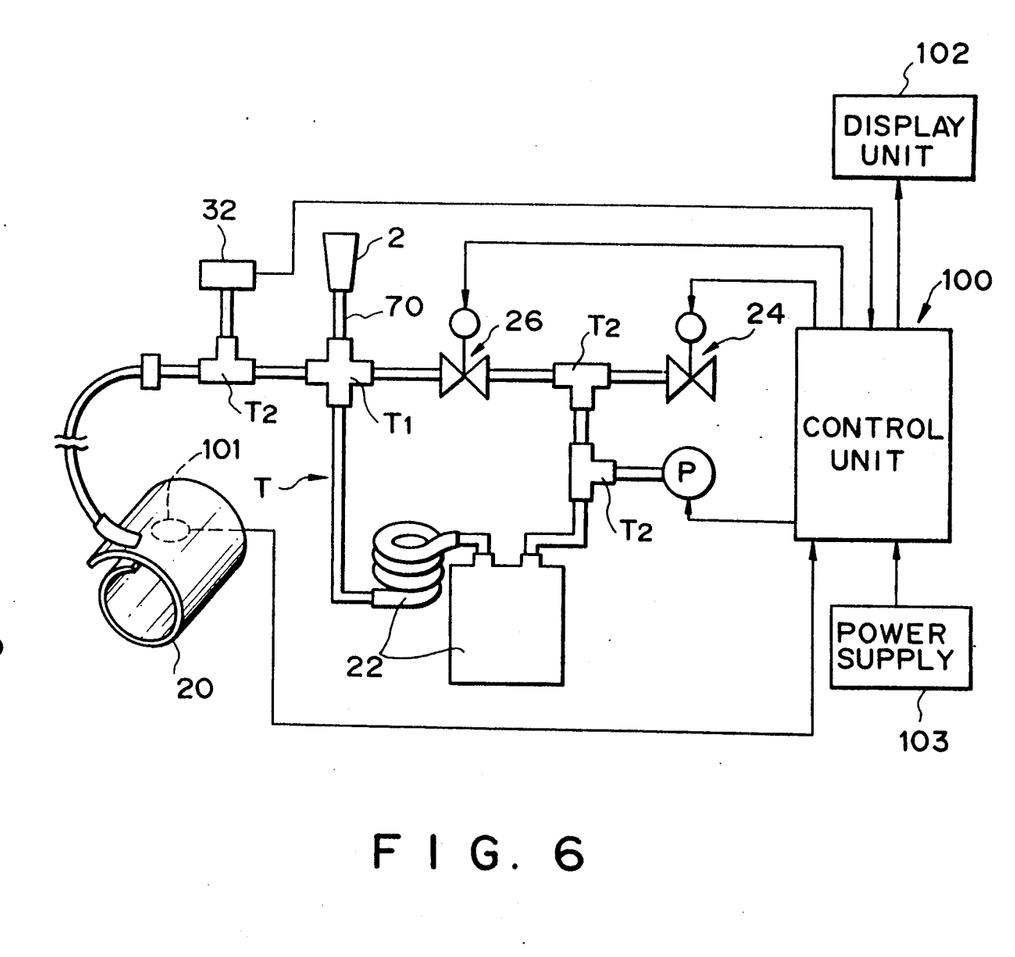
FIG. 6 is a tubing diagram showing a pneumatic system of an automatic sphygmomanometer one circuit element of which is a gas flow valve.

With reference to the tubing diagram of FIG. 6 showing the pneumatic system of an automatic sphygmomanometer, the gas flow valve is provided in the air circuit in such a manner that its pressure-responsive surfaces 2a are directed toward a pump P. The air circuit, which communicates with a cuff 20 and pressure sensor 32, is connected via a four-branch tube junction T1 and two-branch tube junctions T2 of tubing T. As shown in FIG. 6, the tubular body 70 into which the main body 2 is fitted is connected to the upwardly direction portion of the four-branch tube junction T1. The pressure sensor 32 is connected to the leftwardly directed portion of the four-branch tube junction T1 via a two-branch tube junction T2, and the cuff 20 is connected to the leftwardly directed portion of this two-branch tube junction T2.

The outflow port of a filter device 22 comprising a fluidic resistor and a fluidic buffer bag is connected to the downwardly directed portion of the four-branch tube junction T1. A motor-driven pump P is connected to the inflow port of the filter device 22 via a two-branch tube junction T2, a bypass valve 26 having an electromagnetically driven solenoid is connected to the upwardly directed portion of this two-branch tube junction T2 via a two-branch tube junction T2, and a discharge valve 24 having an electromagnetically driven solenoid is similarly connected to the upwardly directed portion of the first-mentioned two-branch tube junction T2 via the second-mentioned two-branch tube junction T2.

A control unit 100 which receives power from a power supply 103 is connected to the pressure sensor 32, the motor-driven pump P and the discharge valve 24 and generates control signals for driving these components. Also connected to the control unit 100 is a microphone 101 (indicated by the dashed line) disposed inside the cuff 20 in order to detect Korotkoff sounds. Specifically, Korotkoff sounds, which find use in measuring blood pressure when the cuff 20 is inflated and deflated, are detected by the microphone 101 and the result is displayed on a display unit 102 comprising an LCD display element.

In the automatic sphygmomanometer thus tubed and wired, the bypass valve 26 is in an open state permitting the passage of air when cuff pressure is less than 20 mmHg. Accordingly, air from the motor-driven pump P flows directly into the cuff 20. When the cuff pressure rises above 20 mmHg, however, the bypass valve 26 assumes a closed state to block the passage of air. Accordingly, air flows through the filter device 22, which is disposed in the pneumatic system extending from the motor-driven pump P to the cuff 20, and which comprises the air resistance element such as a filter and performs the function of a rectifying circuit. As a result, the cuff 20 is supplied with air at a constant rate without cuff pressure pulsation at the time of blood pressure measurement.

Though discharge at a constant rate from the main body 2 takes place gradually even when air is being supplied to the cuff to inflate the same, the amount of air supplied by the motor-driven pump P is much greater in comparison with the amount of discharge from the main body 2; therefore, the discharge from the main body 2 has almost no influence upon the rate of pressure increase.

When cuff is deflated, the motor-driven pump P stops and the air is gradually discharged from the cuff 20 via the main body 2.

Figure 7:
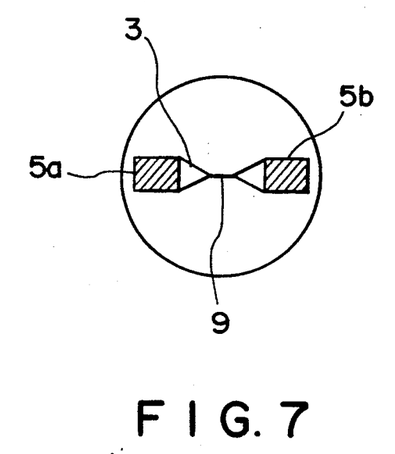
FIG. 7 is an explanatory view showing the state of a slit under application of high pressure.

In a case where the pressure is comparatively high at the beginning of the deflation, the linear slit 3 is forcibly urged in the closing direction in proportion to the magnitude of the pressure since the pressure-responsive surfaces 2a of the main body 2 form a wedge-shaped portion. As a result, the opposite sides of the slit 3 contact each other substantially at their central portions, as shown in FIG. 7, whereby a gap 8 has its opening area reduced.

Figure 8:
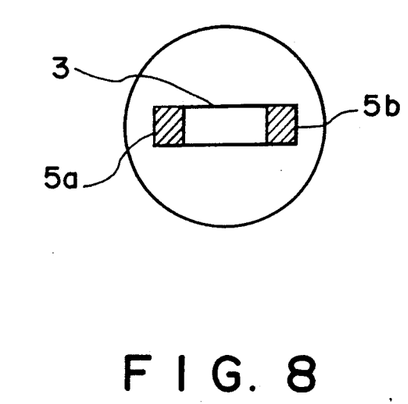
FIG. 8 is an explanatory view showing the state of the slit under application of low pressure.

When the deflation of the cuff 20 of the sphygmomanometer proceeds and eventually reaches a small value, the pressure acting upon the outer sides of the pressure-responsive surfaces 2a of the wedge-shaped portion becomes small, and hence there is a gradual increase in the opening area of the gap 8 forming the gas flow port of the linear slit 3. When pressure declines further, the pressure-responsive surfaces 2a stop being deformed by the pressure, whereupon the main body 2 returns to its original shape, as depicted in FIG. 8. Even though the opening area gradually changes in this manner, a gas flow port is formed between the projections 5a, 5b at the distal end of the flapper 5 and therefore the contacting portions of the slit 3 can be reduced. Furthermore, since both edge portions of the projections 5a, 5b are embraced by the slit portion, the flapper 5 does not move with respect to the slit 3. This makes possible a stabilized flow of air.

Accordingly, at the time of the deflation, a constant rate of pressure decrease is obtained with almost no influence upon the magnitude of the pressure within the sphygmomanometer, thereby making it possible to improve the accuracy of blood pressure measurement. In accordance with the illustrated embodiment, a contact portion 9 occurs substantially at only one location, which is between the projections 5a, 5b at the distal end of the flapper 5.

Here the gas flow valve can be used also in a case where the cuff is inflated by a manually operated rubber baloon.

Figure 9:
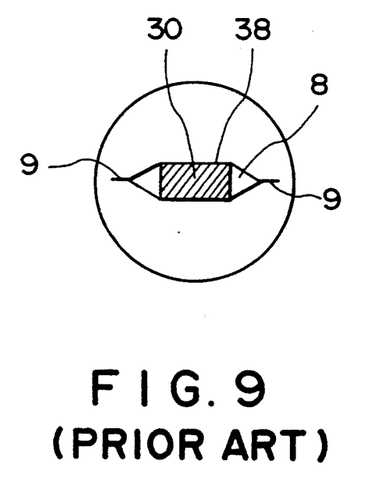
FIG. 9 is an explanatory view showing the state of a slit under application of high pressure in a prior-art example.
Figure 10:
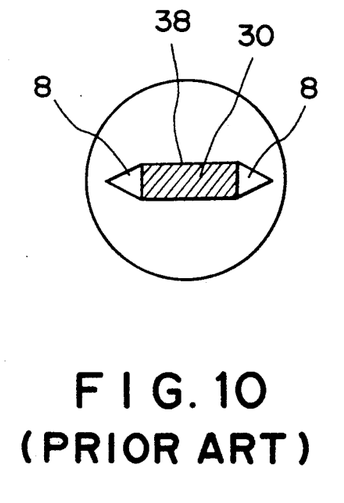
FIG. 10 is an explanatory view showing the state of a slit under application of low pressure in a prior-art example.

In FIG. 9, which is a diagram showing the operation of the prior-art gas flow valve for purposes of comparison, it is evident that the invention differs from the prior art in that contact portions 9 in this example are formed planarly on both sides of the flapper 30. The length of these contact portions causes a large amount of variance in the flow rate of the gas. More specifically, in the prior-art gas flow valve as shown in FIG. 9, many contact portions 9 are produced and the state of contact at these portions tends to fluctuate, as a result of which stable discharge cannot be achieved. In addition, since the flapper 30 is not embraced at both ends of the slit, as shown in FIG. 10, the flapper 30 readily slips to the left and right and the rate of discharge is rendered unstable.

Figure 11:
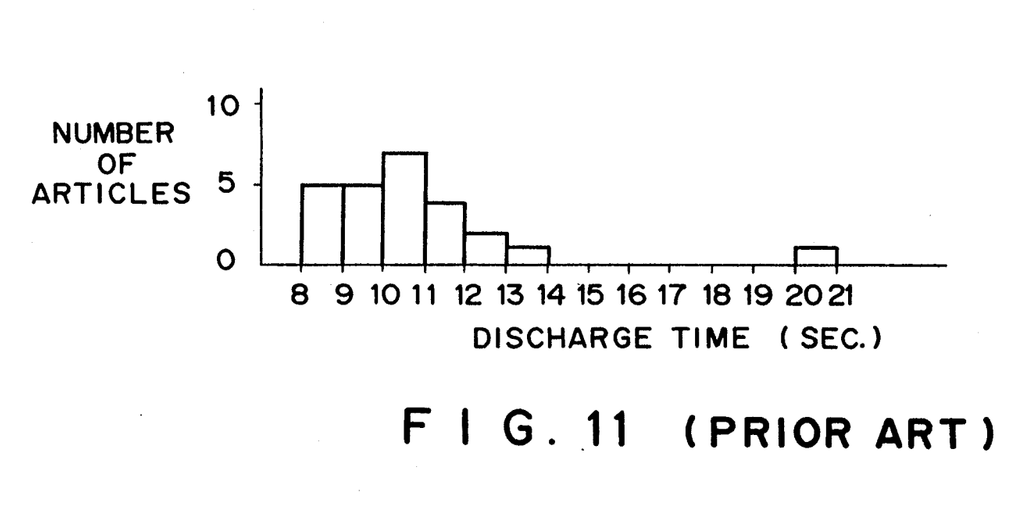
FIG. 11 is a graph showing results of measurement using a conventional article.
Figure 12:
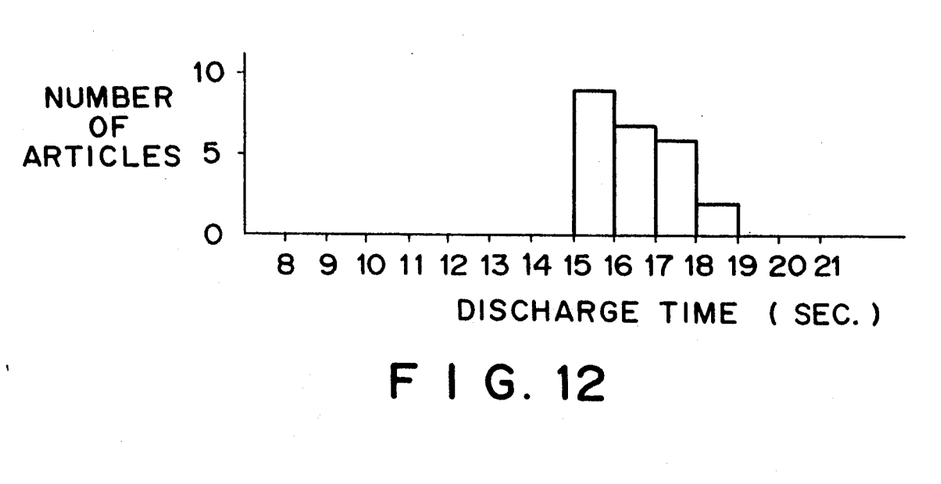
FIG. 12 is a graph showing measurement results using a constant-rate discharge valve of the present embodiment.

FIGS. 11 and 12 are diagrams showing a variance in the length of discharge time among a number of gas flow valves. These diagrams illustrate results obtained by measuring time for discharge from a pressure of 150 mmHg to a pressure of 100 mmHg after the gas flow valve of the present embodiment and the conventional gas flow valve (FIGS. 13-15) was installed in the automatic sphygmomanometer of FIG. 6. To this end, a total of approximately 25 each of the conventional articles and articles of the present invention were sampled and the results tabulated. The results of FIGS. 11 and 12 are shown in the following table:

|  | PRIOR ART | THIS EMBODIMENT |
| --- | --- | --- |
| FASTEST | 8.5 | 15.0 |
| SLOWEST | 20.9 | 18.6 |
| DIFFERENCE | 12.4 | 3.6 |

(Units: seconds)

It will be understood from the foregoing comparison that the variance in length of discharge time is reduced if the gas flow valve of the present invention is employed as a discharge valve. This means that the present invention is not readily influenced by variance due to material characteristics or errors in manufacture and design.

Accordingly, if the valve of the present invention is used as a discharge valve in an automatic sphygmomanometer, it will be possible to construct a system in which the the bleeding of air is uniform, thereby facilitating control.

Thus, in accordance with the present invention as described above, the distal end of a thin, sheet-like member is divided into a plurality of projections and air flow ports are formed between the plurality of projections. As a result, contact portions of the slit can be reduced, and the plurality of projections are embraced by the slit. This makes possible stabilized flow of gas.

As many apparently widely different embodiments of the present invention can be made without departing from the spirit and scope thereof, it is to be understood that the invention is not limited to the specific embodiments thereof except as defined in the appended claims.

What is claimed is:

1. A gas flow valve comprising:
   a resilient main body, adapted to be coupled to a pressure-operated part, said main body being tapered from a base end portion thereof to a distal end portion thereof to form a wedge-shaped portion at said distal end portion, said wedge-shaped portion having pressure-responsive surfaces and a tip at end portions of said pressure-responsive surfaces, said tip of said wedge-shaped portion having a substantially linear elastically deformable slit therein whose degree of opening and closing varies in proportion to a magnitude of pressure applied to said pressure-responsive surfaces;
   a gas flow passageway extending longitudinally within said main body and communicating with said slit, said pressure-responsive surfaces at least partly forming at least a portion of said gas flow passageway; and
   a thin sheet-like member having a plurality of spaced apart projections on a distal end portion thereof and oriented in said gas flow passageway such that said plurality of projections are situated in and are supported in said slit to maintain at least a portion of said slit, between projections, in an open condition;
   wherein at least one gap is formed between said plurality of spaced apart projections in an intermediate portion of said slit between ends of said slit, and said at least one gap serving as at least one gas flow port located between adjacent ones of said plurality of spaced apart projections, and said slit is elastically deformed by a change in pressure of gas flow through said gas flow passageway and applied to said pressure-responsive surfaces, whereby the size of said at least one gas flow port is varied responsive to gas flow pressure so as to provide a stable gas flow velocity through said at least one gas flow port conforming to a change in gas flow pressure applied to said pressure responsive surfaces.

2. The gas flow valve of claim 1, wherein:
said gas flow passageway is an air flow passageway; and
said resilient main body is situated on an end portion of a tubular body through which air flows, said gas flow passageway receiving air flowing through said tubular body.

3. The gas flow valve of claim 2, wherein:
said distal end portion of said thin sheet-like member is bifurcated to form said projections and said projections are held substantially immobile by opposite inner edges of said slit.

4. The gas flow valve of claim 2, wherein said distal end portion of said thin sheet-like member has spaced apart projections which are held substantially immobile by opposite inner edges of said slit, whereby at least one gas flow port is provided in an intermediate portion of said slit.

5. The gas flow valve of claim 2, wherein:
said distal end portion of said thin sheet-like member is bifurcated to form said projections and said projections are held substantially immobile by opposite inner edges of said slit;
said thin sheet-like member has a substantially T-shaped positioning portion for positioning and orienting said thin sheet-like member in said gas flow passageway of said main body; and
said positioning portion is fixedly fitted into at least one groove of said main body.

6. The gas flow valve of claim 5, wherein said at least one groove comprises a pair of grooves in a base end portion of said main body opposite to said distal end portion.

7. The gas flow valve of claim 5, wherein said thin sheet-like member is made of a synthetic resin.

8. The gas flow valve of claim 1, wherein said distal end portion of said thin sheet-like member has spaced apart projections which are held substantially immobile by opposite inner edges of said slit, whereby at least one gas flow port is provided in an intermediate portion of said slit.

9. The gas flow valve of claim 1, wherein:
said distal end portion of said thin sheet-like member is bifurcated to form said projections and said projections are held substantially immobile by opposite inner edges of said slit.

10. The gas flow valve of claim 1, wherein:
said distal end portion of said thin sheet-like member is bifurcated to form said projections and is held substantially immobile by opposite inner edges of said slit;
said thin sheet-like member has a substantially T-shaped positioning portion for positioning and orienting said thin sheet-like member in said gas flow passageway of said main body; and
said positioning portion is fixedly fitted into at least one groove of said main body.

11. The gas flow valve of claim 10, wherein at least one groove comprises a pair of grooves in a base end portion of said main body opposite to said distal end portion.

12. The gas flow valve of claim 10, wherein said thin sheet-like member is made of a synthetic resin.

13. A sphygmomanometer comprising:
a tubing system through which air flows;
a gas flow valve coupled to said tubing system such that said gas flow valve is in air communication with air flowing through said tubing system;
a cuff to which said gas flow valve is connected by said tubing system; and
air feeding means for selectively feeding air into said cuff to inflate said cuff;
said gas flow valve comprising:
a resilient main body, adapted to be coupled to a pressure-operated part, said main body being tapered from a base end portion thereof to a distal end portion thereof to form a wedge-shaped portion at said distal end portion, said wedge-shaped portions having pressure-responsive surfaces and a tip at end portions of said pressure-responsive surfaces, said tip of said wedge-shaped portion having a substantially linear elastically deformable slit therein whose degree of opening and closing varies in proportion to a magnitude of pressure applied to said pressure-responsive surfaces;
a gas flow passageway extending longitudinally within said main body and communicating with said slit, said pressure-responsive surfaces at least partly forming at least a portion of said gas flow passageway; and
a thin sheet-like member having a plurality of spaced apart projections on a distal end portion thereof and oriented in said gas flow passageway such that said plurality of projections are situated in and are supported in said slit to maintain at least a portion of said slit, between projections, in an open condition;
wherein at least one gap is formed between said plurality of spaced apart projections in an intermediate portion of said slit between ends of said slit, and said at least one gap serving as at least one gas flow port located between adjacent ones of said plurality of spaced apart projections, and said slit is elastically deformed by a change in pressure of gas flow through said gas flow passageway and applied to said pressure-responsive surfaces, whereby the size of said at least one gas flow port is varied responsive to gas flow pressure so as to provide a stable gas flow velocity through said at least one gas flow port conforming to a change in gas flow pressure applied to said pressure-responsive surfaces.

14. A sphygmomanometer according to claim 13, wherein
said distal end portion of said thin sheet-like member is bifurcated to form said projections and said projections are held substantially immobile by opposite inner edges of said slit.

15. A sphygmomanometer according to claim 14, further comprising:
control means coupled to said air feeding means for controlling air feed;
blood pressure measuring means, coupled to said control means, for measuring blood pressure;
valve opening/closing means, coupled to said control means, for controlling cuff pressure; and display means, coupled to said control means, for displaying results of measurement performed by said blood pressure measuring means.

16. A sphygmomanometer according to claim 13, wherein said distal end portion of said thin sheet-like member has spaced apart projections which are held substantially immobile by opposite inner edges of said slit, whereby at least one gas flow port is provided in an intermediate portion of said slit.

17. A sphygmomanometer according to claim 16, further comprising:
control means coupled to said air feeding means for controlling air feed;
blood pressure measuring means, coupled to said control means, for measuring blood pressure;
valve opening/closing means, coupled to said control means, for controlling cuff pressure; and
display means, coupled to said control means, for displaying results of measurement performed by said blood pressure measuring means.

18. A sphygmomanometer according to claim 13, wherein said distal end portion of said thin sheet-like member is bifurcated to form said projections and said projections are held substantially immobile by opposite inner edges of said slit;
said thin sheet-like member has a substantially T-shaped positioning portion for positioning and orienting said thin sheet-like member in said gas flow passageway of said main body; and
said positioning portion is fixedly fitted into at least one groove of said main body.

19. A sphygmomanometer according to claim 18, wherein said at least one groove comprises a pair of grooves in a base end portion of said main body opposite to said distal end portion.

20. A sphygmomanometer according to claim 19, further comprising:
control means coupled to said air feeding means for controlling air feed;
blood pressure measuring means, coupled to said control means, for measuring blood pressure;
valve opening/closing means, coupled to said control means, for controlling cuff pressure; and
display means, coupled to said control means, for displaying results of measurement performed by said blood pressure measuring means.

21. A sphygmomanometer according to claim 18, wherein said thin sheet-like member is made of a synthetic resin.

22. A sphygmomanometer according to claim 21, further comprising:
control means coupled to said air feeding means for controlling air feed;
blood pressure measuring means, coupled to said control means, for measuring blood pressure;
valve opening/closing means, coupled to said control means, for controlling cuff pressure; and
display means, coupled to said control means, for displaying results of measurement performed by said blood pressure measuring means.

23. A sphygmomanometer according to claim 18, further comprising:
control means coupled to said air feeding means for controlling air feed;
blood pressure measuring means, coupled to said control means, for measuring blood pressure;
valve opening/closing means, coupled to said control means, for controlling cuff pressure; and
display means, coupled to said control means, for displaying results of measurement performed by said blood pressure measuring means.

24. A sphygmomanometer according to claim 13, further comprising:
control means coupled to said air feeding means for controlling air feed;
blood pressure measuring means, coupled to said control means, for measuring blood pressure;
valve opening/closing means, coupled to said control means, for controlling cuff pressure; and
display means, coupled to said control means, for displaying results of measurement performed by said blood pressure measuring means.

* * * * *

UNITED STATES PATENT AND TRADEMARK OFFICE
CERTIFICATE OF CORRECTION

PATENT NO. : 5,027,823
DATED     : July 2, 1991
INVENTOR(S) : Kohji SANAKA

It is certified that error appears in the above-identified patent and that said Letters Patent is hereby corrected as shown below:

Title page, Section [56] References Cited, insert the following under "FOREING PATENT DOCUMENTS":

-- 61-142003  9/1986  Japan --

Column 1, line 66, following "velocity", insert --.--.

Signed and Sealed this

Sixth Day of April, 1993

Attest:

STEPHEN G. KUNIN

*Attesting Officer*   Acting Commissioner of Patents and Trademarks